(12) United States Patent
White et al.

(10) Patent No.: US 11,364,183 B2
(45) Date of Patent: Jun. 21, 2022

(54) COSMETIC SYSTEM CONTAINING AN APPLICATOR AND A GEL COMPOSITION

(71) Applicant: L'ORÉAL, Paris (FR)

(72) Inventors: Geoffrey David White, Old Bridge, NJ (US); Lemis Noya Tarajano, Brooklyn, NY (US)

(73) Assignee: L'ORÉAL, Paris (FR)

( * ) Notice: Subject to any disclaimer, the term of this patent is extended or adjusted under 35 U.S.C. 154(b) by 410 days.

(21) Appl. No.: 15/967,297

(22) Filed: Apr. 30, 2018

(65) Prior Publication Data
US 2019/0328627 A1 Oct. 31, 2019

(51) Int. Cl.
| | | |
|---|---|---|
| *A61K 8/04* | (2006.01) | |
| *A61K 8/81* | (2006.01) | |
| *A61K 8/19* | (2006.01) | |
| *A61K 8/58* | (2006.01) | |
| *A61K 8/88* | (2006.01) | |
| *A61K 8/42* | (2006.01) | |
| *A45D 34/04* | (2006.01) | |
| *A61K 8/34* | (2006.01) | |

(52) U.S. Cl.
CPC .............. *A61K 8/042* (2013.01); *A45D 34/04* (2013.01); *A61K 8/19* (2013.01); *A61K 8/34* (2013.01); *A61K 8/42* (2013.01); *A61K 8/585* (2013.01); *A61K 8/8152* (2013.01); *A61K 8/88* (2013.01); *A45D 2200/1018* (2013.01); *A45D 2200/1045* (2013.01); *A61K 2800/30* (2013.01); *A61K 2800/33* (2013.01); *A61K 2800/34* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 4,050,826 A | 9/1977 | Berghahn et al. | |
| D401,850 S | 12/1998 | Srinaul | |
| 7,427,412 B1 | 9/2008 | Painter et al. | |
| D620,368 S | 7/2010 | Pedersen | |
| 8,444,337 B2 | 5/2013 | Teller | |
| D709,652 S | 7/2014 | Teller | |
| D734,895 S | 7/2015 | Liu | |
| 9,198,840 B1 | 12/2015 | Goldman | |
| 10,117,497 B1 * | 11/2018 | Murphy | ............... A45D 34/00 |
| 2003/0129016 A1 | 7/2003 | Gueret | |
| 2006/0159734 A1 | 7/2006 | Shudo | |
| 2007/0077331 A1 | 4/2007 | Kiefer et al. | |
| 2008/0083419 A1 | 4/2008 | Glenn et al. | |
| 2008/0107747 A1 | 5/2008 | Roederer | |
| 2011/0091531 A1 * | 4/2011 | Furrer | ..................... A61K 8/64 |
| | | | 424/450 |
| 2012/0076850 A1 | 3/2012 | Shudo | |
| 2013/0337032 A1 | 12/2013 | Shudo | |
| 2014/0332026 A1 | 11/2014 | Peters et al. | |
| 2016/0081889 A1 | 3/2016 | Romos-Stanbury et al. | |
| 2017/0000720 A1 * | 1/2017 | Fujita | ....................... A61K 8/86 |
| 2017/0266087 A1 | 9/2017 | Bouarfa et al. | |

FOREIGN PATENT DOCUMENTS

| | | |
|---|---|---|
| DE | 20 2012 104 020 | 12/2012 |
| EP | 0 155 350 | 9/1985 |
| EP | 1 565 326 B1 | 10/2008 |
| RU | 128 078 | 5/2018 |
| WO | WO 2005/079746 | 9/2005 |
| WO | WO 2006/073767 A1 | 7/2006 |
| WO | WO2013117551 A1 * | 8/2013 |
| WO | WO 2014/166716 A1 | 10/2014 |

OTHER PUBLICATIONS

U.S. Appl. No. 15/885,380, filed Jan. 31, 2018, Geoffrey D. White.
"Dow Corning,® VM-2270 Aerogel Fine Particles" Dow Corning, http://www2.dowcorning.com/DataFiles/090007c88020e235.pdf, XP002650585, 2009, 5 pages.

\* cited by examiner

*Primary Examiner* — Robert A Wax
*Assistant Examiner* — Randeep Singh
(74) *Attorney, Agent, or Firm* — Oblon, McClelland, Maier & Neustadt, L.L.P.

(57) ABSTRACT

The present invention relates to a cosmetic system comprising an applicator and a gel composition, and methods for making-up and enhancing the appearance of keratinous materials using the systems.

18 Claims, 1 Drawing Sheet

COSMETIC SYSTEM CONTAINING AN APPLICATOR AND A GEL COMPOSITION

FIELD OF THE INVENTION

The present invention relates to a cosmetic system comprising an applicator and a gel composition.

DISCUSSION OF THE BACKGROUND

U.S. Pat. No. 7,427,412, RU 128078, U.S. Pat. No. 4,050,826, EP 155350, US 2003/0129016, US 2014/0332026, US 2008/0083419, EP 1565326, DE 202012104020, U.S. Pat. No. 8,444,337, U.S. D 734,895, U.S. D 620,368, U.S. D 709,652, and U.S. D 401850 relate to delivery devices for formulations.

Although such delivery devices are known, there remains a need for improved ways and systems to make-up and enhance the appearance of keratinous materials using gel compositions which can have difficulty flowing through delivery devices, which can preclude application of product using a delivery device owing to clogging, and which can have poor powder dispersion.

Accordingly, one aspect of the present invention is a cosmetic system comprising an applicator and a gel composition which addresses one or more issues identified in the previous paragraph.

SUMMARY OF THE INVENTION

The present invention relates to a cosmetic system comprising an applicator and a gel composition.

The present invention relates to a cosmetic system comprising (1) an applicator comprising a container and at least one porous material in the container, and (2) a gel composition.

The present invention relates to a cosmetic system comprising (1) an applicator comprising a container and at least one porous material in the container, wherein the porous material has different pore sizes in different portions of the material, and (2) a gel composition.

The present invention relates to a cosmetic system comprising an applicator and a gel composition which (1) is thick enough to suspend powders, (2) has a sol/gel point low enough to allow it to flow through the porous material (where such movement is preferably via a capillary effect), and/or (3) does not re-gel or re-thicken if the composition dries and is subsequently exposed to water.

The present invention relates to a cosmetic system comprising an applicator and a gel composition comprising (1) at least one C2-C5 alcohol, (2) at least one silica aerogel, (3) at least one powder, (4) at least one amphiphilic polymer and/or (5) at least one cooling agent. Preferably, the gel composition is free of, or substantially free of, coloring agents, oils, silicones, surfactants and/or film formers.

The present invention relates to a cosmetic system comprising (a) an applicator comprising a container and at least one porous material in the container, and (b) a gel composition which (1) is thick enough to suspend powders, (2) has a sol/gel point low enough to allow it to flow through the porous material (where such movement is preferably via a capillary effect), and/or (3) does not re-gel or re-thicken if the composition dries and is subsequently exposed to water.

The present invention relates to a cosmetic system comprising (a) an applicator comprising a container and at least one porous material in the container, and (b) a gel composition comprising (1) at least one C2-C5 alcohol, (2) at least one silica aerogel, (3) at least one powder, (4) at least one amphiphilic polymer and/or (5) at least one cooling agent. Preferably, the gel composition is free of, or substantially free of, coloring agents, oils, silicones, surfactants and/or film formers.

The present invention relates to a cosmetic system comprising (a) an applicator comprising a container and at least one porous material in the container, wherein the porous material has different pore sizes in different portions of the material, and (b) a gel composition which (1) is thick enough to suspend powders, (2) has a sol/gel point low enough to allow it to flow through the porous material (where such movement is preferably via a capillary effect), and/or (3) does not re-gel or re-thicken if the composition dries and is subsequently exposed to water.

The present invention relates to a cosmetic system comprising (a) an applicator comprising a container and at least one porous material in the container, wherein the porous material has different pore sizes in different portions of the material, and (b) a gel composition comprising (1) at least one C2-C5 alcohol, (2) at least one silica aerogel, (3) at least one powder, (4) at least one amphiphilic polymer and/or (5) at least one cooling agent. Preferably, the gel composition is free of, or substantially free of, coloring agents, oils, silicones, surfactants and/or film formers.

The present invention also relates to methods for enhancing the appearance of a keratinous material comprising using the applicator of the cosmetic system of the present invention to apply the gel composition of the cosmetic system to keratinous material.

The present invention also relates to methods for making-up a keratinous material comprising using the applicator of the cosmetic system of the present invention to apply the gel composition of the cosmetic system to keratinous material.

It is to be understood that both the foregoing general description and the following detailed description are exemplary and explanatory only, and are not restrictive of the invention.

DETAILED DESCRIPTION OF THE INVENTION

According to the invention, the term "devoid of" a particular material refers to a composition not containing any of the particular material. So, for example, a composition "devoid of" surfactant does not contain any surfactant, and a composition "devoid of" oil does not contain any oil. Similarly, a composition "free of" surfactant contains 0.25% by weight of the composition or less of surfactant, and a composition "free of" oil contains 0.25% by weight of the composition or less of oil. And, a composition "substantially free of" surfactant contains 1% by weight of the composition or less of surfactant, and a composition "substantially free of" oil contains 1% by weight of the composition or less of oil.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

"Film former" or "film forming agent" or "film forming polymer" or "film forming resin" as used herein mean a polymer or resin that leaves a film on the substrate to which it is applied, for example, after a solvent accompanying the film former has evaporated, absorbed into and/or dissipated on the substrate.

"Transfer resistance" as used herein refers to the resistance of a color cosmetic composition from being removed from its site of application, in particular a keratinous material such as skin or lips. An example of a suitable testing protocol to determine if topcoat compositions have a positive or negative effect on the transfer-resistance of a color cosmetic composition is as follows: a 1 mil film of color cosmetic (e.g., foundation) is applied to scrub paper, and allowed to dry overnight in a 37° C. oven. The film is then placed on an automatic draw-down machine set-up with a draw-down rod that has loop Velcro strips attached to it. 5-6 trials can be run, with a standard included (e.g., a gel composition devoid of powders). A small amount of sample is placed onto the film in front of a Velcro piece, and 6 passes across the film are made. After 6 passes have been made, the trials are rated vs. the standard using the following scale: 1-2 (removal worse); 3 (removal equal); 4-5 (removal better).

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

As used herein a range of ratios is meant to include every specific ratio within, and combination of subranges between the given ranges.

"Keratinous materials" includes materials containing keratin such as hair, skin, eyebrows, lips and nails.

"Volatile", as used herein, means having a flash point of less than about 100° C.

"Non-volatile", as used herein, means having a flash point of greater than about 100° C.

"Gel Crossover Point" (Sol/Gel Point), means the point at which the G" (loss modulus) intersects the G' (storage modulus), reported in % strain. It is the point at which a composition goes from a more solid state to a more liquid state. An example of a method for determining gel crossover point is as follows: a Discovery HR-2 Rheometer by TA Instruments can be used, having 40 mm parallel plate geometry on a stainless steel flat peltier plate. The test can be run @ 20° C., with test parameter of angular frequency of 1.0 rad/s and logarithmic sweep: Strain % 0.01 to 1000.0%. 5 points per decade. Results reported in % strain. The compositions, systems and methods of the present invention can comprise, consist of, or consist essentially of the essential elements and limitations of the invention described herein, as well as any additional or optional ingredients, components, or limitations described herein or otherwise useful.

Cosmetic Systems

According to the present invention, cosmetic systems comprising at least one gel composition and at least one applicator are provided. Parenthetical numerical references relate to corresponding elements in FIGS. 1 and 2.

Applicator

Figure 1:
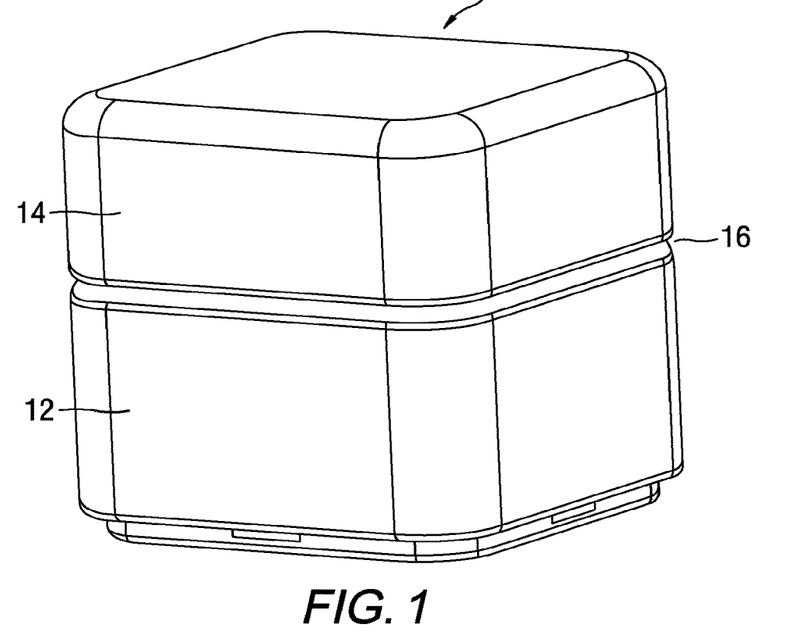
FIG. 1 depicts an example of a container of the present invention.
Figure 2:
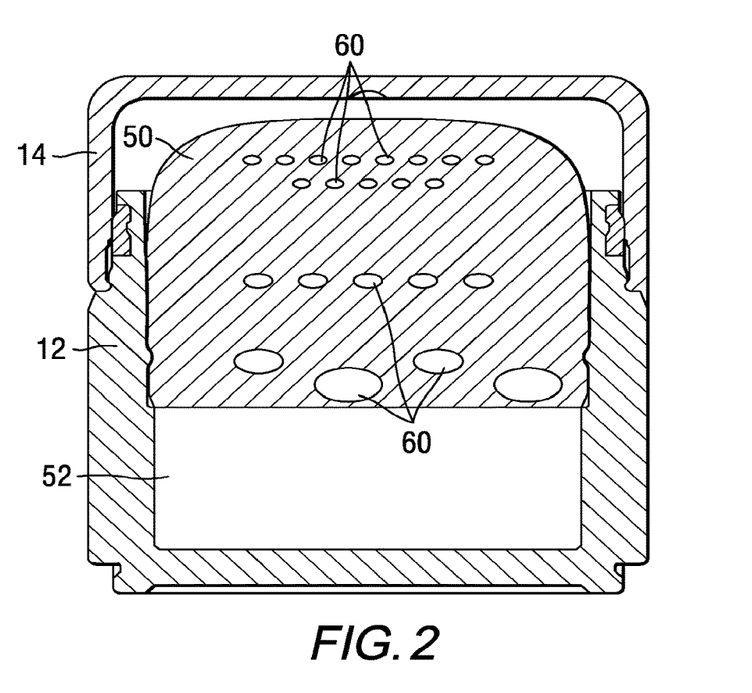
FIG. 2 is a cross-section of an applicator of the present invention comprising a base portion of the container, a cap of the container, a storage reservoir, and a porous material.

According to the present invention, cosmetic systems of the present invention comprise at least one applicator. According to preferred embodiments, the applicator comprises a container (10) and at least one porous material (50) in the container (10).

According to preferred embodiments, the container (10) can be made of any substance suitable for housing the porous material such as, for example, plastic, glass, metal, wood, etc. Further, the container substance can be hard (does not deform upon application of pressure), resilient (slightly deforms upon application of pressure but returns to its original form after application pressure stops) or soft (deforms upon application of pressure). And, cross-sections of the container can be of shape such as, for example, square, rectangular, circular, elliptical, oval, etc.

According to preferred embodiments, the container is of a size and shape which can be held comfortably and/or ergonomically in a hand during application. For example, preferred containers comprise a cross-section having a width of 1.5 cm to 4.5 cm and a length of 1.5 cm to 4.5 cm, preferably a width of 2 cm to 4 cm and a length of 2 cm to 4 cm, and preferably a width of 2.5 cm to 3.5 cm and a length of 2.5 cm to 3.5 cm, including all ranges and subranges therebetween. According to preferred embodiments, the length and width of the container (cross-section) are in the shape of a square, and have a length and width of about 2.5 cm to about 3 cm. Such preferred embodiments as described in this paragraph can provide a combination of quick application of product and ability to reach sensitive areas like skin under the eyes and around the nose.

According to preferred embodiments, the container comprises a base portion (12) and a cap (14). During use of the cosmetic systems of the present invention, the cap (14) is removed from the base portion (12) to expose the porous material (50) in the base portion (12), and the porous material (50) is contacted with keratinous material as described more fully below. The cap (14) can be detachable from the base portion (12), or the cap (14) can be connected to the base portion (12) through a hinge or other known attachment structure (16).

According to preferred embodiments, the porous material (50) can either be removable (for example, in a reusable system) or not removable (for example, in a single use system) from the base portion (12) of the container (10).

According to preferred embodiments, the porous material (50) has different sizes of pores (60) in different portions of the material. Preferably, the porous material (50) has a pore (60) size gradient in which pore size increases from one side or portion of the material to the opposite side or portion of the material. Preferably, as depicted in FIG. 2, the porous material has a pore size gradient which goes from large pore size at the side or portion of the porous material at the bottom of the base portion of the container (that is, the side or portion of the porous material facing the bottom of the base portion of the container) to small pore size at the side or portion of the porous material to be contacted with keratinous material (that is, the side or portion of the porous material facing outward from the base portion of the container). Such a gradient can be made, for example, by serially combining layers of different, desired porosities, or by sintering or molding materials at specific rates, temperatures and pressure as is known in the art.

According to preferred embodiments, the porous material can be made through cast-molding processes as is known in the art. Preferably, if the porous material is made through cast-molding processes, the surface of the mold used to cast and mold the porous material has a texture depth of 0.03 inches or less, including all ranges and subranges therebetween such as, for example, less than 0.01 inches, less than 0.0005 inches, from about 0.01 inches to about 0.03 inches, and from about 0.0001 inches to about 0.01 inches. Preferably, the texture corresponds to that of MT11000 according to the Moldtech book standard. Preferred methods of making the porous material include the processes set forth in U.S. Pat. No. 6,030,558, the entire contents of which is hereby incorporated by reference.

Although not wanting to be bound by any particular theory, it is currently believed that the preferred pore size differences described above allow for the gel composition to move from the base portion of the container to the portion of the porous material to be contacted with keratinous material through wicking and/or capillary action.

According to preferred embodiments, the portion of the porous material to be contacted with keratinous material has an average pore size of about 30 to 80 microns, preferably about 35 to 75 microns, preferably about 40 to 70 microns, and preferably about 45 to 65 microns, including all ranges and subranges therebetween. Preferably, the portion of the porous material to be contacted with keratinous material constitutes no more than half (50%) of the porous material, preferably no more than a third (33%) of the porous material, and preferably no more than a quarter (25%) of the porous material.

According to preferred embodiments, the portion of the porous material at the bottom of the base portion of the container has an average pore size of about 90 to 200 microns, preferably about 95 to 190 microns, preferably about 100 to 170 microns, and preferably about 110 to 160 microns, including all ranges and subranges therebetween.

Preferably, the portion of the porous material at the bottom of the base portion of the container constitutes no more than bottom half (50%) of the porous material, preferably no more than a third (33%) of the porous material, and preferably no more than a quarter (25%) of the porous material.

It is to be understood that the porous material may optionally further contain one or more mid-portions between the portion at the bottom of the base portion of the container and the portion to be contacted with keratinous material. Preferably, the one or more mid-portions contain average pore size(s) between those in the portion of the porous material at the bottom of the base portion of the container and those in the portion of the porous material to be contacted with keratinous material. However, it should be understood that it is not necessary that the average pore size(s) in the mid-portion(s), if present, are between the pore sizes of the other portions of the porous material.

According to preferred embodiments, the porous material is soft and/or not abrasive. Preferably, the porous material is a porous polymeric material, or a sponge-like material. Preferably, the porous material is made out of one or more thermoplastic polymers. Suitable examples of such thermoplastic polymers include, but are not limited to, polyethylene (PE), polypropylene (PP), polyethylene terephthalate (PET), polytetrafluoroethylene (PTFE), ethyl vinyl acetate (EVA), polyvinylidene fluoride (PVDF), polycarbonate (PC), acrylnitrile-butadiene-styrene (ABS), and mixtures thereof. Particularly preferred thermoplastic polymers include low density polyethylene (for example, polyethylene having a density range of 0.910-0.940 g/cm$^3$) and polyethylene terephthalate.

Also preferably, to improve soft and/or non-abrasive properties of the porous material, the porous material has rounded edges. According to preferred embodiments, the porous material can also act as a reservoir for the gel composition. Preferably, the porous material contains enough gel composition to deliver product for at 30 days, preferably at least 60 days, and preferably at least 90 days.

According to preferred embodiments of the present invention, the applicator further contains a storage reservoir (52) for the gel composition. If present, the storage reservoir (52) is preferably located between the base portion of the container (12) and the porous material (50) and is in contact with the porous material (50) such that the storage reservoir supplies gel composition to the porous material (50).

Preferably, the storage reservoir is a porous, low-density layer of compressed fibers which stores gel composition. Preferably, the fibers are made out of one or more thermoplastic polymers. Suitable examples of such thermoplastic polymers include, but are not limited to, polyethylene (PE), polypropylene (PP), polyethylene terephthalate (PET), polytetrafluoroethylene (PTFE), ethyl vinyl acetate (EVA), polyvinylidene fluoride (PVDF), poly carbonate (PC), acrylnitrile-butadiene-styrene (ABS), and mixtures thereof. Particularly preferred thermoplastic polymers include low density polyethylene (for example, polyethylene having a density range of 0.910-0.940 g/cm$^3$) and polyethylene terephthalate.

According to preferred embodiments, the compressed fibers have a density from about 0.04 g/cc to about 0.08 g/cc, preferably from about 0.05 g/cc to about 0.07 g/cc, and preferably about 0.06 g/cc. Also preferably, the compressed fibers are capable of holding about 67% to about 85% of its volume in gel composition, preferably about 70% to about 83%, and preferably from about 77% to about 82%, including all ranges and subranges therebetween.

Gel Composition

According to the present invention, the cosmetic systems of the present invention comprise a gel composition.

According to preferred embodiments, the gel composition of the present application (1) is thick enough to suspend powders, (2) has a sol/gel point low enough to allow it to flow through the porous material (where such movement is preferably via wicking and/or a capillary effect), and/or (3) does not re-gel or re-thicken if the composition dries and is subsequently exposed to water. Preferably the gel compositions of the present invention possess at least two of these properties. Preferably, the gel compositions of the present invention comprise all three of these properties.

By suspending powders, a stable gel composition comprising dispersed powders can be obtained. By having a low sol/gel point, the gel compositions of the present invention need less shear to transform the composition from a solid gel state to a liquid state, thereby providing the compositions with the ability to move through the porous material. By not re-gelling or re-thickening, the gel compositions of the present invention do not prevent application of the gel compositions using the porous material owing to clogging of the pores.

According to preferred embodiments, the gel compositions have a gel crossover point ranging from about 35% to about 85% strain, preferably from about 40% to about 80% strain, and preferably from about 45% to about 75% strain, including all ranges and subranges therebetween. According to preferred embodiments, when the gel composition of the present invention is applied to a color cosmetic composition, the gel composition does not inhibit the transfer-resistance of the color cosmetic composition. For purposes of the present invention, the "color cosmetic composition" referred to herein can be any suitable cosmetic composition containing at least one coloring agent which can provide color to a keratinous material to which it has been applied.

According to preferred embodiments, the gel compositions of the present invention are devoid of, free of, or substantially free of oils.

According to preferred embodiments, the gel compositions of the present invention are devoid of, free of, or substantially free of surfactants.

According to preferred embodiments, the gel compositions of the present invention are devoid of, free of, or substantially free of silicones.

According to preferred embodiments, the gel compositions of the present invention are devoid of, free of, or substantially free of film formers.

According to preferred embodiments, the gel compositions of the present invention are devoid of, free of, or substantially free of coloring agents.

According to preferred embodiments, the gel compositions of the present invention are devoid of, free of, or substantially free of at least one of coloring agents, oils, surfactants, silicones and film formers; preferably at least two of coloring agents, oils, surfactants, silicones and film formers; preferably at least three of coloring agents, oils, surfactants, silicones and film formers; preferably at least four of coloring agents, oils, surfactants, silicones and film formers and preferably of all five of coloring agents, oils, surfactants, silicones and film formers.

According to preferred embodiments, the gel compositions of the present invention comprise one or more of the following ingredients.

C2-C5 Alcohol and Water (Hydro-Alcoholic Solvent Component)

According to the present invention, the gel compositions may comprise at least one C2-C5 alcohol. Suitable C2-C5 alcohols include ethanol, propanol, butanol, pentanol, isopropanol, isobutanol and isopentanol. Ethanol is particularly preferred.

Preferably, the C2-C5 alcohol(s) is/are present in the gel compositions of the present invention in amounts ranging from about 0.5% to about 30%, preferably from about 1% to about 25%, and preferably from about 2.5% to about 20%, by weight, based on the total weight of the composition, including all ranges and subranges in between.

According to preferred embodiments, the gel compositions of the present invention further comprise water. Preferably, the gel compositions comprise from about 5% to about 90% water, preferably from about 20% to about 85% water, preferably from about 50% to about 85% water, and preferably from about 60% to about 80% water by weight, based on the total weight of the composition, including all ranges and subranges therebetween.

Preferably, the solvent component of the gel compositions of the present invention consists essentially of, or consists of, water and C2-C5 alcohols. That is, the composition does not contain any solvent in an amount which has a material adverse effect on the transfer-resistance properties of a color cosmetic composition to which it has been applied.

Silica Aerogel

According to the present invention, the gel composition may comprise at least one silica aerogel. Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990. Silica aerogels, in general, have been disclosed in U.S. Pat. No. 9,320,689, the entire contents of which is hereby incorporated by reference.

Preferably, the aerogels used according to the present invention are hydrophobic silica aerogels. The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalized the OH groups with silyl groups Si—Rn, for example trimethylsilyl groups. Hydrophobic silica aerogels particles surface-modified with trimethylsilyl groups (trimethylsilyl silica) are preferred. As regards the preparation of hydrophobic silica aerogels particles that have been surface-modified by silylation, reference may be made to document U.S. Pat. No. 7,470,725, the entire contents of which is hereby incorporated by reference.

Suitable examples of hydrophobic silica aerogels that may be used in accordance with the present invention include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references AEROGEL TLD 201, AEROGEL OGD 201, AEROGEL TLD 203, ENOVA® AEROGEL MT 1100. ENOVA AEROGEL MT 1200.

In particular, the aerogel sold under the name VM-2270 (INCI name: Silica silylate), by the company Dow Corning, the particles of which have a mean size ranging from 5-15 microns and a specific surface area per unit of mass ranging from 600 to 800 m²/g can be used.

Preferably, the silica aerogel(s) is/are present in the gel compositions of the present invention in amounts ranging from about 0.05% to about 10% by weight, preferably from 0.075% to 5% by weight, and preferably from 0.1% to 1% by weight, including all ranges and subranges therebetween, all weights based on the weight of the composition as a whole.

Powder

According to the present invention, the gel compositions may comprise at least one powder. According to preferred embodiments, the gel composition comprises at least two powders.

"Powders" should be understood as meaning solid particles which are insoluble in the medium of the composition, whatever the temperature at which the composition is manufactured.

The powders can be colorless or white and inorganic or organic, of any physical shape (platelet, spherical or oblong) and of any crystallographic form (for example sheet, cubic, hexagonal, orthorhombic and the like). The powders can be porous or nonporous.

Mention may also be made, as powders, of particles of mineral, vegetable or organic origin. Thus, use may be made, for example, of polyethylene beads or powder, such as those sold under the name Microthene MN 727 or Microthene MN 710-20 by Equistar or such as the powders sold under the name Gotalene 120 Colorless 2 by Dupont; thermoplastic powders such as Nylon particles, such as the Nylon-12 sold by Arkema under the name Orgasol 2002 Exd Nat Cos; powders from inorganic materials such as perlite; poly(vinyl chloride) powder; pumice (INCI name) such as pumice 3/B from Eyraud; ground fruit kernel shells, such as ground materials derived from apricot kernels or walnut shells; sawdust, wood flour or cork flour; glass beads; alumina (aluminium oxide) (INCI name: Alumina), such as the product sold under the name Dermagrain 900 by Marketech International; sugar crystals; beads which melt during application on the skin, such as, for example, spheres based on mannitol and cellulose which are sold under the Unisphere names by Induchem, agar-based capsules which are sold under the Primasponge names by Cognis and spheres based on jojoba esters which are sold under the Floraspheres names by Floratech; and their mixtures.

Mention may also be made, as powders, of particles which are organic or inorganic microspheres. Mention may be made, as spherical organic powders, for example, polyethylene powders; polytetrafluoroethylene (Teflon®) powders; microspheres based on acrylic copolymers, such as those made of ethylene glycol dimethacrylate/lauryl methacrylate copolymer sold by Dow Corning under the Polytrap name; expanded powders, such as hollow microspheres and in particular the microspheres sold under the Expancel name by Kemanord Plast or under the name Micropearl F 80 ED by Matsumoto; silicone resin microbeads, such as those sold under the Tospearl name by Toshiba Silicone; polymethyl methacrylate microspheres, sold under the name Microsphere M-100 by Matsumoto or under the name Covabead LH85 by Wackherr; ethylene/acrylate copolymer powders, such as those sold under the Flobeads name by Sumitomo Seika Chemicals; powders formed of natural organic materials, such as starch powders, in particular powders formed of maize, wheat or rice starch, which are or are not crosslinked, such as powders formed of starch crosslinked with octenylsuccinic anhydride, sold under the Dry-Flo name by National Starch; metal soaps derived from organic carboxylic acids having from 8 to 22 carbon atoms, preferably from 12 to 18 carbon atoms, for example zinc stearate, magnesium stearate, lithium stearate, zinc laurate or magnesium myristate; Polypore®L 200 (Chemdal Corporation); silicone resin microbeads (Tospearl® from Toshiba, for example); polyurethane powders, in particular powders formed of crosslinked polyurethane comprising a copolymer, the said copolymer comprising trimethylol hexyllactone, such as the hexamethylene diisocyanate/trimethylol hexyllactone polymer sold under the name Plastic Powder D-400® or Plastic Powder D-800® by Toshiki; carnauba microwaxes, such as that sold under the name MicroCare 350® by Micro Powders; synthetic wax microwaxes, such as that sold under the name MicroEase 114S® by Micro Powders; microwaxes composed of a mixture of carnauba wax and polyethylene wax, such as those sold under the names Micro Care 300® and 310® by Micro Powders; microwaxes consisting of a mixture of carnauba wax and synthetic wax, such as that sold under the name Micro Care 325® by Micro Powders; or polyethylene microwaxes, such as those sold under the names Micropoly 200®, 220®, 220L® and 250S® by Micro Powders.

According to preferred embodiments, the gel composition comprises at least one inorganic powder and at least one spherical powder.

According to preferred embodiments, the gel composition comprises at least one inorganic powder and at least one thermoplastic powder.

According to preferred embodiments, the gel composition comprises Nylon-12 particles and polymethyl methacrylate particles.

Preferably, the powder(s) is/are present in the gel compositions of the present invention in amounts ranging from about 0.1% to about 10%, preferably from about 0.25% to about 7.5%, and preferably from about 0.5% to about 5%, by weight, based on the total weight of the composition, including all ranges and subranges in between.

Preferably, the weight ratio of powder to silica aerogel present in the gel compositions of the present invention ranges from about 15:1 to about 1:5, preferably from about 10:1 to about 1:3, and preferably from about 2:1 to about 1:2, including all ranges and subranges therebetween.

Preferably, the total combined amount of powder(s) and silica aerogel(s) present in the gel compositions of the present invention is less than 12% by weight with respect to the total weight of the composition, including preferred ranges from about 1% to about 10%, preferably from about 2% to 8%, preferably from about 3% to about 7%, and preferably from about 4% to about 6% by weight, based on the total weight of the composition, including all ranges and subranges therebetween.

Cooling Agent

According to preferred embodiments, the gel composition may comprise at least one cooling agent in an amount sufficient to provide a cooling effect to the keratinous material to which the gel composition is applied. Whether a cooling effect is provided or not is a binary issue which is readily discernible by the user of the gel composition based on typical experience with cooling sensations. According to preferred embodiments, the cooling agent is methyl diisopropyl propionamide.

According to preferred embodiments, the cooling effect provided by the cooling agent remains for at least 1 minute after application of the gel composition, preferably at least 2 minutes, preferably at least 3 minutes, and preferably at least 5 minutes, and can last as long as 10 minutes after application.

According to preferred embodiments, the cooling agent is present in the gel composition compositions of the present invention in an amount ranging from about 0.05% to about 3% by weight, preferably from about 0.075% to about 1% by weight, and preferably from about 0.1% to about 0.5% by weight, based on the total weight of the composition, including all ranges and subranges therebetween.

Amphiphilic Polymers

According to preferred embodiments, the gel compositions may comprise at least one amphiphilic polymer. Preferably, the amphiphilic polymer comprises at least one ethylenically unsaturated monomer containing a sulphonic group, in freeform or partially or totally neutralized form and comprising at least one hydrophobic portion. The hydrophobic portion present in these polymers preferably contains from 6 to 50 carbon atoms, preferably from 6 to 22 carbon atoms, preferably from 6 to 18 carbon atoms and preferably from 12 to 18 carbon atoms, including all ranges and subranges therebetween.

The amphiphilic polymers may be based on at least one ethylenically unsaturated hydrophilic monomer A and on at least one hydrophobic monomer B. Preferably, the monomer A comprises a strong acid function, in particular a sulphonic acid or phosphonic acid function. The hydrophobic monomer B comprises at least one hydrophobic radical, chosen from: saturated or unsaturated $C_6$-$C_{18}$ linear alkyl radicals (for example, n-hexyl, n-octyl, n-decyl, n-hexadecyl, n-dodecyl or oleyl); branched alkyl radicals (for example, isostearic) or cyclic alkyl radicals (for example, cyclododecane or adamantane); $C_6$-$C_{18}$ fluoro or alkylfluoro radicals (for example, the group of formula $(CH_2)_2$—$(CF_2)_9$—$CF_3$); a cholesteryl radical or radicals derived from cholesterol (for example, cholesteryl hexanoate); aromatic polycyclic groups, for instance naphthalene or pyrene; and silicone or alkylsilicone or alkylfluorosilicone radicals. Among these radicals, linear and branched alkyl radicals are preferred.

The amphiphilic polymers are preferably water-soluble or water-dispersible in neutralized form. Their viscosity at a concentration of 1% in water, at a shear rate of 1 s$^{-1}$, at a pH of between 5 and 8, at 25° C., is preferably less than 5,000 mPa·s. Amphiphilic polymers suitable for use in the present invention are described in US 2001/049419 and U.S. Pat. No. 6,645,476, the entire contents of both of which are hereby incorporated by reference.

The amphiphilic polymers may be crosslinked. The crosslinking agents may be chosen from, for example, the polyolefinically unsaturated compounds commonly used for crosslinking polymers obtained by free-radical polymerization. According to one preferred embodiment of the invention, the crosslinking agent is chosen from methylenebisacrylamide, allyl methacrylate or trimethylolpropane triacrylate (TMPTA). The degree of crosslinking preferably ranges from 0.01 mol % to 10 mol %, and preferably from 0.2 mol % to 2 mol %, relative to the polymer, including all ranges and subranges therebetween.

Preferred amphiphilic polymers are chosen from crosslinked or noncrosslinked amphiphilic polymers polymers of 2acrylamido-2-methylpropanesulphonic (AMPS) acid and of at least one ethylenically unsaturated monomer comprising at least one hydrophobic portion containing from 6 to 30 carbon atoms, preferably from 6 to 22 carbon atoms, preferably from 6 to 18 carbon atoms and preferably from 12 to 18 carbon atoms, including all ranges and subranges therebetween.

The amphiphilic polymers can be partially or totally neutralized with a mineral base (for example, sodium hydroxide, potassium hydroxide or aqueous ammonia) or an organic base such as monoethanolamine, diethanolamine, triethanolamine, aminomethylpropanediol, N-methylglucamine, or basic amino acids, for instance arginine and lysine, and mixtures thereof.

Suitable examples of amphiphilic polymers include, but are not limited to, hydrophobically-modified sulfonic acid copolymers such as Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant) (crosslinked ethoxylated AMPS/behenyl methacrylate), Ammonium Acryloyldimethyltaurate/Steareth-25 Methacrylate Crosspolymer (Aristoflex HMS) (ethoxylated copolymer of AMPS/stearyl methacrylate crosslinked with trimethylol triacrylate), Aristoflex SNC (crosslinked ethoxylated AMPS/C16-C18), Aristoflex LNC (noncrosslinked AMPS/C12-C14), and mixtures thereof.

Preferably, the amphiphilic polymer(s) is/are present in the gel compositions of the present invention in amounts ranging from about 0.05% to about 5% by weight, preferably from 0.1% to 1% by weight, and preferably from 0.2% to 0.5% by weight, including all ranges and subranges therebetween, all weights based on the weight of the composition as a whole.

Film-Forming Agents

According to preferred embodiments, the gel compositions may optionally further comprise at least one film-forming agent. Preferably, if a film-forming agent is present in the gel composition, the film-forming agent is a silicone film-forming agent selected from the group consisting of silicone resins, polyorganosiloxane copolymers, and mixtures thereof. Also preferably, the silicone resin is selected from the group consisting of siloxysilicate resins, silsesquioxane resins, and mixtures thereof.

Volatile Solvent

The compositions of the invention may optionally further comprise at least one volatile solvent.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

The at least one volatile solvent, if present, is generally present in the compositions of the present invention in an amount ranging from about 5% to about 50% by weight; such as from about 10% to about 45% by weight; such as from about 15% to about 40% by weight, all weights being based on the weight of the composition as a whole.

Non-Volatile Solvent

The compositions of the present invention may optionally further comprise at least one non-volatile solvent.

The volatility of the solvents can be determined using the evaporation speed as set forth in U.S. Pat. No. 6,338,839, the content of which is herein incorporated by reference.

Non-volatile solvents include low viscosity oils (having a viscosity from about 5 to about 10 centipoise) and high viscosity oils (having a viscosity of from about 100 to about 10,000 centipoise), and mixtures thereof.

According to a particular embodiment of the present invention, the oil is a high viscosity oil which is a silicone oil and/or a hydrocarbon oil. "High viscosity" means an oil having a viscosity greater than 100 cSt, particularly greater than 250 cSt at 25° C. Most particularly, the non-volatile oil is selected from a silicone oil. Such oils are described, for example in US 2011/0293550 and US 2004/0126350, both of which are herein incorporated by reference.

Non-limiting examples of suitable non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes (CTFA designation "dimethicones") comprising alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C.

Specific examples of suitable for this invention high viscosity silicone oils include, but are not limited to, Xiameter® silicone fluids from Dow Corning.

Wax

The gel compositions of the present invention may optionally further comprise at least one wax.

Coloring Agent (Colorant)

The compositions of the present invention may optionally further comprise at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Miscellaneous Additives

The compositions of the present invention may optionally further comprise at least one cosmetically or dermatologically acceptable additive such as thickener, a plasticizer, an antioxidant, an essential oil, a botanical extract, a fragrance, a preserving agent, a fragrance, a pasty fatty substance, a neutralizing agent, and a polymer, and cosmetically active agents and/or dermatological active agents such as, for example, emollients, moisturizers, vitamins, essential fatty acids and medicaments.

According to preferred embodiments, the gel compositions of the present invention comprise:

from about 0.1% to about 0.5% by weight of methyl diisopropyl propionamide;

from about 2.5% to about 20% by weight of ethanol;

from about 60% to about 80% by weight of water;

from about 0.1% to about 1% by weight of at least one silica silylate;

from about 0.5% to about 5% by weight of total combined amount of at least two powders, preferably Nylon-12 and polymethyl methacrylate; and from about 0.2% to about 0.5% by weight of Acryloyldimethyltaurate/Steareth-25 Methacrylate Crosspolymer.

According to preferred embodiments, the gel compositions of the present invention comprise:

from about 0.1% to about 0.5% by weight of methyl diisopropyl propionamide;

from about 2.5% to about 20% by weight of ethanol;

from about 60% to about 80% by weight of water;

from about 0.1% to about 1% by weight of at least one silica silylate;

from about 0.5% to about 5% by weight of total combined amount of at least two powders, preferably Nylon-12 and polymethyl methacrylate; and from about 0.2% to about 0.5% by weight of Acryloyldimethyltaurate/Steareth-25 Methacrylate Crosspolymer, wherein the total combined amount of powder(s) and silica aerogel(s) present in the gel compositions of the present invention is less than 12% by weight with respect to the total weight of the composition, and wherein the weight ratio of powder to silica aerogel present in the gel compositions of the present invention ranges from about 2:1 to about 1:2.

According to preferred embodiments, gel compositions comprising (1) at least one C2-C5 alcohol, (2) at least one silica aerogel and (3) at least one powder are provided. Preferably, the gel composition is free of, or substantially free of, coloring agents, oils, silicones, surfactants and/or film formers. Preferably, the gel composition further comprises at least one amphiphilic polymer and/or at least one cooling agent. Preferably, when the gel composition is applied to a color cosmetic composition, the gel composition does not inhibit the transfer-resistance of the color cosmetic composition.

According to preferred embodiments, methods for enhancing the appearance of a keratinous material comprising using the applicator of the cosmetic system of the present invention to apply the gel composition of the cosmetic system to keratinous material are provided. According to preferred embodiments, the gel compositions of the present invention comprise (1) at least one C2-C5 alcohol, (2) at least one silica aerogel and (3) at least one powder. Preferably, the gel composition is free of, or substantially free of, coloring agents, oils, silicones, surfactants and/or film formers. Preferably, the gel composition further comprises at least one amphiphilic polymer and/or at least one cooling agent. Preferably, when the gel composition is applied to a color cosmetic composition, the gel composition does not inhibit the transfer-resistance of the color cosmetic composition.

According to preferred embodiments, methods for making-up a keratinous material comprising using the applicator of the cosmetic system of the present invention to apply the gel composition of the cosmetic system to keratinous material are provided. According to preferred embodiments, the gel compositions of the present invention comprise (1) at least one C2-C5 alcohol, (2) at least one silica aerogel and (3) at least one powder. Preferably, the gel composition is free of, or substantially free of, coloring agents, oils, silicones, surfactants and/or film formers. Preferably, the gel composition further comprises at least one amphiphilic polymer and/or at least one cooling agent. Preferably, when the gel composition is applied to a color cosmetic composition, the gel composition does not inhibit the transfer-resistance of the color cosmetic composition.

According to preferred embodiments, the cosmetic systems of the present invention allow for application of reproducible amounts of gel composition to keratinous material during use. Preferably, the cosmetic systems allow for application of about 0.008 mg to 0.1 mg per dab or stroke of the porous material on keratinous material, preferably about 0.01 mg to 0.07 mg per dab or stroke, preferably about 0.01 mg to 0.05 mg per dab or stroke, and preferably about 0.01 mg to 0.03 mg per dab or stroke, including all ranges and subranges therebetween.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The present invention will be better understood from the examples which follow. The examples are intended to be nonrestrictive and explanatory only, with the scope of the invention defined by the claims.

Example 1—Invention Compositions

The following composition can be prepared:

| INCI US | INVENTION COMPOSITION. |
|---|---|
| AMMONIUM ACRYLOYLDIMETHYLTAURATE/STEARETH-25 METHACRYLATE CROSSPOLYMER | 0.3-0.5 |
| PERLITE | 0.6-0.8 |
| SILICA SILYLATE | 0.2-0.4 |
| NYLON-12 | 1.6-2.0 |
| METHYL DIISOPROPYL PROPIONAMIDE | 0.05-0.2 |
| ALCOHOL DENAT. | 15-20 |
| WATER | 70-80 |
| POLYMETHYL METHACRYLATE | 1.5-2.5 |

Example 2—Amount of Product Applied

Protocol: 15 g of the formula of example 1 was placed into a 2 oz jar, and a porous polymeric material was placed into the 2 oz jar, and allowed to sit overnight. The porous polymeric material was then then applied to the skin 10 times, and the amount of product lost from the porous polymeric material during application was weighed.

Two different applicators were tested: one applicator having a porous material with a top portion having average pore size of about 40 microns; and one applicator having a porous material with a top portion having average pore size of about 100 microns.

The first applicator (pore size of about 40 microns) deposited 0.001 g/dab, which was perceived favorably upon application. The second applicator (pore size of about 100 microns) deposited 0.003 g/dab, which was perceived as being too heavy/too much product deposited.

Example 3—Comparison of Wicking or Capillary Effect of Gel Compositions

Identical compositions were prepared, except the invention composition contained 0.5% Aristoflex HMS and the comparative composition contained 0.5% Carbopol. Both gels were thick, with the invention composition having a higher viscosity.

However, when placed at the base of a porous polymeric material having a bottom porosity of 100-170 micron and a top porosity of 40-75 micron, the comparative composition (Carbopol) did not flow via capillary effect to the top portion of the porous polymeric material. Surprisingly, the invention composition (Aristoflex HMS) did flow through the porous polymeric material via capillary effect. The invention composition (Aristoflex HMS) had a sol/gel crossover point of about 45%, whereas the comparative composition (Carbopol) had a sol/gel crossover point of about 110%. The lower sol/gel point associated with the present invention resulted in low strain, allowing the Aristoflex HMS gel to become a fluid, allowing for flow through the porous polymeric material. In contrast, the comparative Carbopol gel remained in a solid state, preventing it from flowing via capillary effect.

Example 4—Comparison of Wicking or Capillary Effect of Gel Compositions

Gels were made using different thickeners. 15 g of each gel was placed into a 2 oz jar, along with an applicator with porous material with a top portion having average pore size of about 40 microns, and a bottom portion having average pore size of about 100 micron. The gels were then observed to see when they wicked through the applicators, and ranked in order of fastest (1) to slowest (5).

| Ingredient | Rank |
| --- | --- |
| Carbomer (0.5%) | 5 |
| Ammonium polyacryloyldimethyl taurate (0.3%) | 4 |
| Acrylates copolymer (3.58%) | 3 |
| Ammonium acryloyldimethyl taurate/steareth-25 methacrylate crosspolymer (0.3%) | 2 |
| Sodium acrylates copolymer and lecithin (0.375%) | 1 |

What is claimed is:

1. A cosmetic system comprising (a) an applicator comprising a container and at least one porous material in the container, wherein the porous material has different pore sizes in different portions of the material, and (b) a gel composition having a sol/gel point low enough to allow it to become fluid such that it flows through the porous material via wicking or capillary effect, wherein the gel composition has a gel crossover point ranging from about 35% to about 85% strain, wherein the gel composition comprises:
   about 0.5% to about 30% by weight of ethanol,
   about 50% to about 85% by weight of water,
   about 0.075% to about 5% by weight of silica silylate,
   about 0.075% to about 1% by weight of methyl diisopropyl propionamide, and
   about 0.1% to about 1% by weight of at least one amphiphilic polymer selected from the group consisting of crosslinked or noncrosslinked polymers of 2-acrylamido-2-methylpropanesulphonic acid and of at least one ethylenically unsaturated monomer comprising at least one hydrophobic portion containing from 6 to 22 carbon atoms,
   all weights being based on the total weight of the gel composition, and
   wherein the gel composition is free of oils.

2. The cosmetic system of claim 1, wherein the gel composition does not re-gel or re-thicken if the composition dries and is subsequently exposed to water.

3. The cosmetic system of claim 1, wherein the gel composition is substantially free of coloring agents, surfactants or film formers.

4. The cosmetic system of claim 1, wherein the gel composition is substantially free of coloring agents, surfactants and film formers.

5. The cosmetic system of claim 1, wherein the applicator further comprises a storage reservoir.

6. The cosmetic system of claim 1, wherein the gel composition comprises at least one inorganic powder and at least one thermoplastic powder.

7. The cosmetic system of claim 1, wherein the gel composition comprises at least two powders which are Nylon-12 particles and polymethyl methacrylate particles.

8. The cosmetic system of claim 1, wherein the powder(s) is/are present in the gel compositions in amounts ranging from about 0.1% to about 10%.

9. The cosmetic system of claim 6, wherein the weight ratio of powder to silica silylate present in the gel compositions ranges from about 15:1 to about 1:5.

10. The cosmetic system of claim 1, wherein the gel composition has a gel crossover point ranging from about 40% to about 80% strain.

11. The cosmetic system of claim 1, wherein the gel composition comprises at least one amphiphilic polymer selected from the group consisting of Ammonium Acryloyldimethyltaurate/VP Copolymer, Ammonium Acryloyldimethyltaurate/Beheneth-25 Methacrylate Crosspolymer, Ammonium Acryloyldimethyltaurate/Steareth-25 Methacrylate Crosspolymer, crosslinked ethoxylated AMPS/C16-C18, noncrosslinked AMPS/C12-C14, and mixtures thereof.

12. The cosmetic system of claim 1, wherein the porous material has a pore size gradient which goes from large pore size at a portion of the porous material in the bottom of a base portion of the container to small pore size at a portion of the porous material to be contacted with keratinous material.

13. The cosmetic system of claim 12, wherein the portion of the porous material to be contacted with keratinous material has an average pore size of about 30 to 80 microns, and the portion of the porous material at the bottom of the base portion of the container has an average pore size of about 90 to 200 microns.

14. The cosmetic system of claim 12, wherein the portion of the porous material to be contacted with keratinous material has an average pore size of about 40 to 70 microns, and the portion of the porous material at the bottom of the base portion of the container has an average pore size of about 100 to 170 microns.

15. The cosmetic system of claim 1, wherein the container is hard.

16. The cosmetic system of claim 1, wherein the gel composition further comprises at least one compound selected from the group consisting of moisturizers and plasticizers.

17. The cosmetic system of claim 1, wherein the gel composition comprises:
- about 2.5% to about 20% by weight of ethanol,
- about 60% to about 80% by weight of water,
- about 0.1% to about 1% by weight of silica silylate,
- about 0.1% to about 0.5% by weight of methyl diisopropyl propionamide, and
- about 0.2% to about 0.5% by weight of at least one amphiphilic polymer selected from the group consisting of crosslinked or noncrosslinked polymers of 2-acrylamido-2-methylpropanesulphonic acid and of at least one ethylenically unsaturated monomer comprising at least one hydrophobic portion containing from 6 to 22 carbon atoms,
- all weights being based on the total weight of the gel composition.

18. A method for enhancing the appearance of a keratinous material comprising applying the gel composition of claim 1 to a keratinous material using the applicator of claim 1.

* * * * *